(12) United States Patent
Leparmentier et al.

(10) Patent No.: US 8,979,859 B2
(45) Date of Patent: Mar. 17, 2015

(54) DEPTH OF IMPACTION

(75) Inventors: Richard Leparmentier, Fort Lauderdale, FL (US); Brian Schmitz, Fort Lauderdale, FL (US); Renen Bassik, Miami, FL (US); Chunyan Wu, Parkland, FL (US); Jason Wojcik, Weston, FL (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 197 days.

(21) Appl. No.: 13/174,755

(22) Filed: Jun. 30, 2011

(65) Prior Publication Data

US 2012/0209277 A1    Aug. 16, 2012

Related U.S. Application Data

(60) Provisional application No. 61/422,556, filed on Feb. 14, 2011.

(51) Int. Cl.

| | |
|---|---|
| *A61B 17/58* | (2006.01) |
| *A61B 17/60* | (2006.01) |
| *A61F 2/00* | (2006.01) |
| *A61B 19/00* | (2006.01) |
| *A61F 2/34* | (2006.01) |
| *A61B 17/92* | (2006.01) |

(52) U.S. Cl.
CPC ............. *A61B 19/5244* (2013.01); *A61F 2/34* (2013.01); *A61B 19/2203* (2013.01); *A61B 2017/922* (2013.01); *A61B 2019/2207* (2013.01); *A61B 2019/2292* (2013.01); *A61B 2019/462* (2013.01); *A61B 2019/562* (2013.01)
USPC .......................................................... 606/91

(58) Field of Classification Search
USPC ............. 606/91, 102, 130; 600/595; 623/914, 623/22.21
See application file for complete search history.

(56) References Cited

U.S. PATENT DOCUMENTS

| | | | |
|---|---|---|---|
| 2008/0255584 A1* | 10/2008 | Beverland et al. | 606/130 |
| 2008/0312663 A1* | 12/2008 | Haimerl et al. | 606/130 |
| 2010/0016860 A1 | 1/2010 | McCardel | |
| 2011/0082587 A1 | 4/2011 | Ziaei et al. | |

OTHER PUBLICATIONS

J.A. D'Antonio, 4.2 Acetabular Positioning to Maximize Range of Motion, www.ceramtec.com, 2005.

* cited by examiner

*Primary Examiner* — Andrew Yang
*Assistant Examiner* — Diana S Jones
(74) *Attorney, Agent, or Firm* — Miller, Matthias & Hull LLP (57) ABSTRACT

A method for determining a depth of impaction of a prosthetic cup into an acetabulum using an end effector and a movable impactor shaft is provided, wherein the prosthetic cup may be positioned at a distal end of the impactor shaft. The method may position the distal end of the impactor shaft at a known pose relative to the end effector, track a spatial pose of the end effector relative to a spatial pose of the acetabulum, determine a spatial pose of the prosthetic cup based on the spatial pose of the end effector and the known pose between the distal end of the impactor shaft and the end effector, and determine the depth of impaction based on the spatial pose of the prosthetic cup and the spatial pose of the acetabulum.

9 Claims, 11 Drawing Sheets

DEPTH OF IMPACTION

CROSS-REFERENCE TO RELATED APPLICATION

This is a non-provisional patent application claiming priority under 35 U.S.C. 119(e) to U.S. Provisional Patent Application Ser. No. 61/442,556, filed on Feb. 14, 2011.

TECHNICAL FIELD

The present disclosure generally relates to surgical systems, and more particularly, to computer-aided systems and methods for joint replacement surgery.

BACKGROUND

Figure 1:
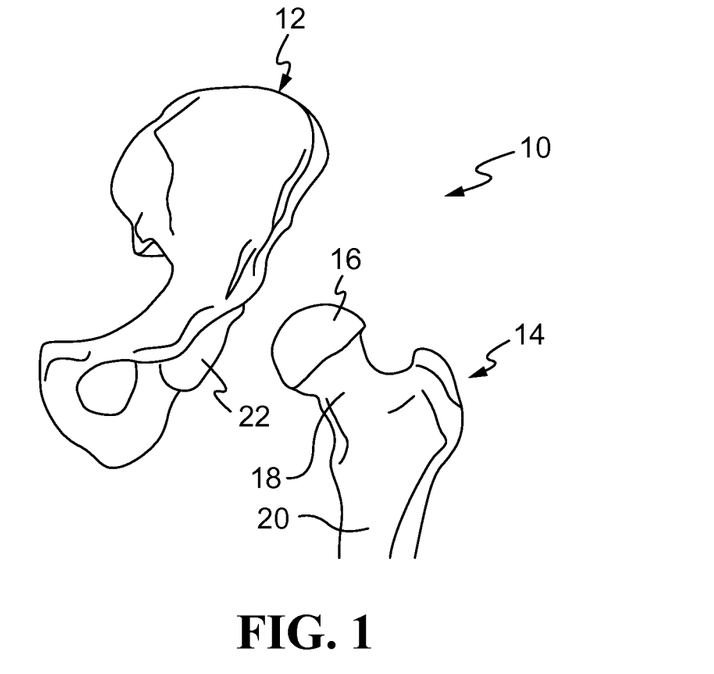
FIG. 1 is a graphical view of a hip joint.
Figure 2:
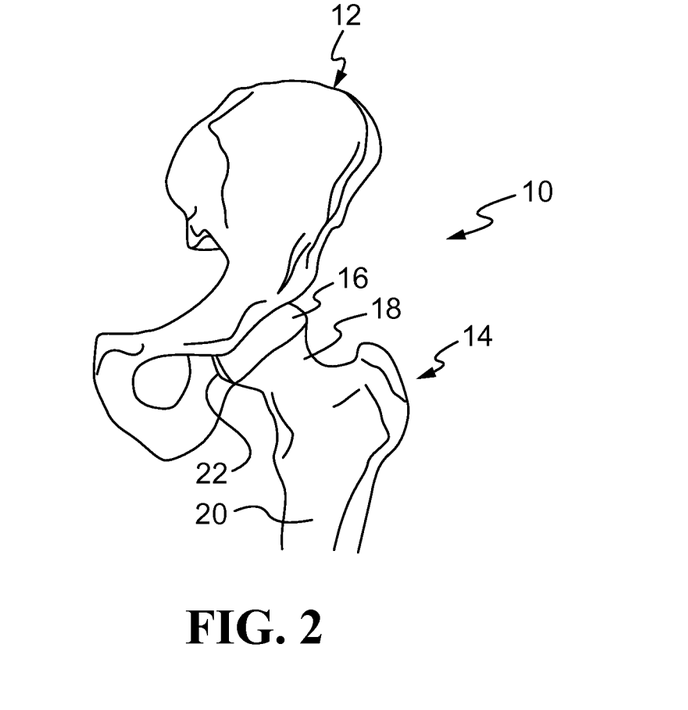
FIG. 2 is another graphical view of a hip joint.

Surgical procedures for correcting, resecting or replacing joints are frequently performed in the medical field. One of the more commonly performed procedures pertains to corrective surgery of the hip joint. Specifically, the diagram of FIG. 1 illustrates the bones of a hip joint 10 including the pelvis 12 and a proximal end of the femur 14. The proximal end of the femur 14 includes a femoral head 16 disposed on a femoral neck 18. The femoral neck 18 connects the femoral head 16 to a femoral shaft 20. As shown in FIG. 2, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10.

Figure 3:
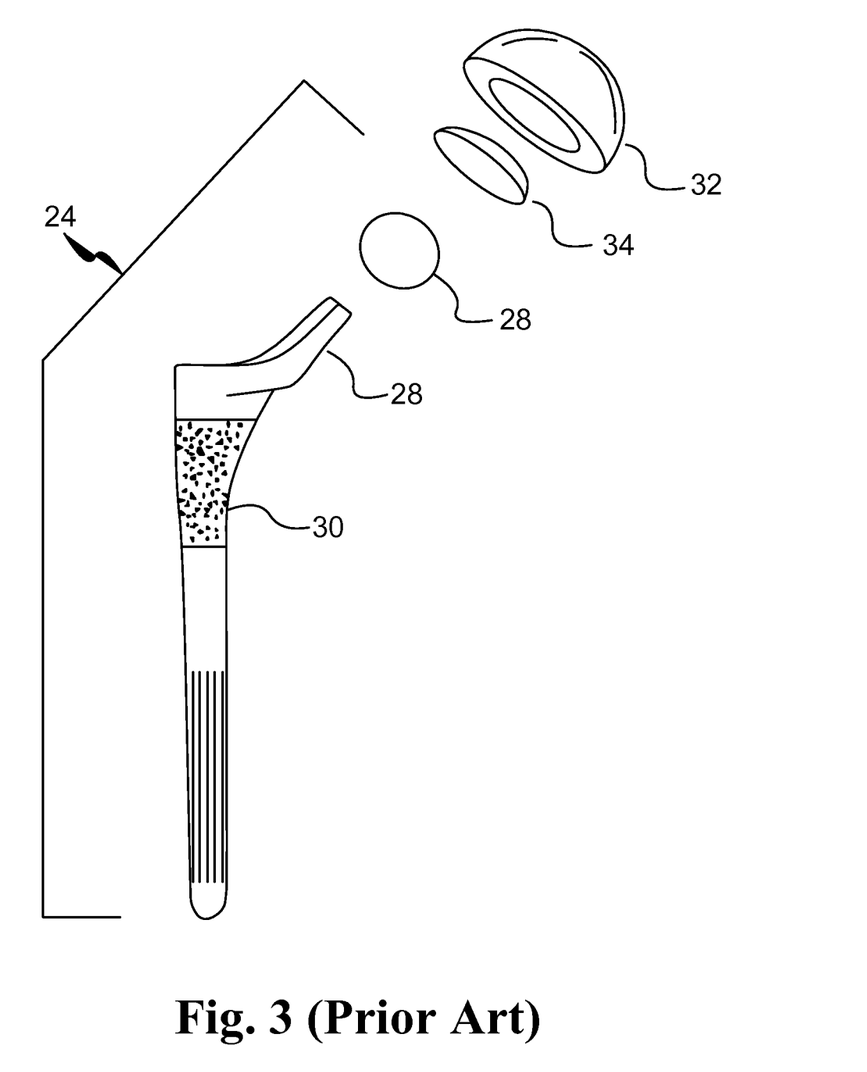
FIG. 3 is a perspective view of prosthetic joint components of the prior art.

Over time, the hip joint 10 may degenerate resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the natural bone with a prosthetic femoral component 24 comprising a head 26, a neck 28 and a stem 30, as shown for example in FIG. 3. Alternatively, if the disease is confined to the natural acetabulum 22 of the pelvis 12, the surgeon resurfaces the acetabulum 22 using a reamer and replaces the natural surface with a prosthetic acetabular component including, for example, the hemispherical shaped cup 32 of FIG. 3 that may include a liner 34. To install the prosthetic cup 32, the surgeon connects the cup 32 to a distal end of an impactor tool or shaft and implants the cup 32 into the reamed acetabulum 22 by repeatedly striking a proximal end of the impactor shaft with a mallet. If the prosthetic cup 32 includes a liner 34, the surgeon snaps the liner 34 into the cup 32 after implanting the cup 32. Depending on the position in which the surgeon places the patient for surgery, the surgeon may use a straight or offset reamer to ream the acetabulum 22 and a straight or offset impactor to implant the prosthetic cup 32. For example, a surgeon that uses a postero-lateral approach may prefer straight reaming and impaction whereas a surgeon that uses an antero-lateral approach may prefer offset reaming and impaction.

Figure 4:
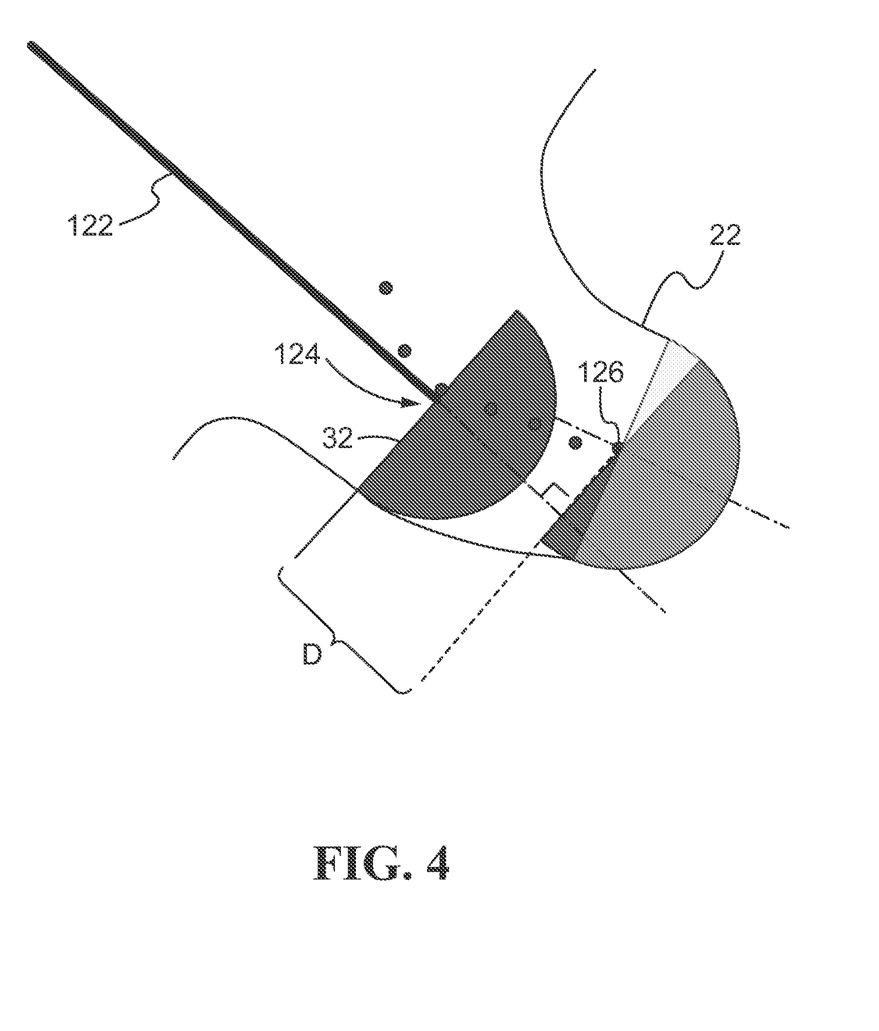
FIG. 4 is a cross-sectional view of a prosthetic cup being impacted into the acetabulum.

A surgeon performing such procedures is met with a variety of difficulties due to the limited visibility and access to the diseased area. While reaming the acetabulum 22, the surgeon must be able to carefully monitor the trajectory of the reamer such that only the appropriate portions the acetabulum 22 are reamed according to plan. Likewise, during impaction of the prosthetic cup 32, as shown in FIG. 4, the surgeon must continuously monitor the trajectory as well as the depth of impaction D such that the cup 32 is adequately seated according to plan. Accordingly, surgeons may rely on computer-aided or robot-guided systems to help them more intuitively plan for the surgical procedures at hand. More specifically, computer-aided systems may enable the surgeons to graphically model the pathologic joint using medical images, such as computer tomography (CT) scans, and the like. Once a plan or model is generated, the surgeon may then view the model on a display screen in the operating room as guidance while performing the actual tasks. However, even with computer-aided and robot-guided systems, the surgeon may be unable to accurately monitor the actual trajectory and depth of the reamer or impactor. Moreover, the surgeon may be unable to accurately determine if the actual trajectory or depth is skewed from the original plan and if any corrections are needed to compensate for the skewed trajectory.

Accordingly, there is a need for improved systems or methods that further facilitate surgical procedures involving at least the hip joint. In particular, there is a need for a system or method that continuously provides the surgeon with more accurate and timely feedback regarding the trajectory as well as the depth of a reamer or a prosthetic cup, while still maintaining all of the benefits associated with computer-aided or robot-guided surgical systems. More specifically, there is a need for a system or method that is able to more readily compare the current progress of a surgical procedure with an original plan and offer corrective visual feedback for any detected diversion from the surgical plan.

SUMMARY OF THE DISCLOSURE

In one aspect of the present disclosure, a method for determining a depth of impaction of a prosthetic cup into an acetabulum using an end effector and a movable impactor shaft is provided, wherein the prosthetic cup is positioned at a distal end of the impactor shaft. The method may position the distal end of the impactor shaft at a known pose relative to the end effector, track a spatial pose of the end effector relative to a spatial pose of the acetabulum, determine a spatial pose of the prosthetic cup based on the spatial pose of the end effector and the known pose between the distal end of the impactor shaft and the end effector, and determine the depth of impaction based on the spatial pose of the prosthetic cup and the spatial pose of the acetabulum.

In another aspect of the disclosure, a method for determining a depth of impaction of a prosthetic cup into an acetabulum using an end effector and a movable impactor shaft is provided, wherein the prosthetic cup is positioned at a distal end of the impactor shaft. The method may track a spatial pose of the acetabulum, track a spatial pose of the end effector, position the distal end of the impactor shaft at a known pose relative to the end effector, determine a spatial pose of the prosthetic cup based on the spatial pose of the end effector and the known pose between the end effector and the distal end of the impactor shaft, register at least the spatial pose of the prosthetic cup and the spatial pose of the acetabulum to at least one medical image of the acetabulum, and determine the depth of impaction based on the spatial pose of the prosthetic cup and the spatial pose of the acetabulum.

In yet another aspect of the disclosure, a system for determining a depth of impaction of a prosthetic cup into an acetabulum is provided. The system may include an end effector, an impactor shaft movably coupled to the end effector, a tracking device configured to track a spatial pose of the end effector and a spatial pose of the acetabulum, and a computing device in communication with at least the tracking device. A distal end of the impactor shaft may be configured to receive the prosthetic cup and extend a predefined distance from the end effector in a default position. The computing device may include at least a controller configured to receive the spatial pose of the end effector and the spatial pose of the acetabulum, determine a spatial pose of the prosthetic cup based on the spatial pose of the end effector and the predefined distance between the impactor shaft and the end effector, register at least the spatial pose of the prosthetic cup and spatial pose of the acetabulum to a medical image of the acetabulum, and determine the depth of impaction based on the spatial pose of the prosthetic cup and the spatial pose of the acetabulum.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make certain references to orthopedic procedures involving hip joints, it should be understood that the subject matter described herein may be applicable to other joints in the body, such as, for example, shoulders, elbows, wrists, spines, knees, ankles, and the like.

Figure 5:
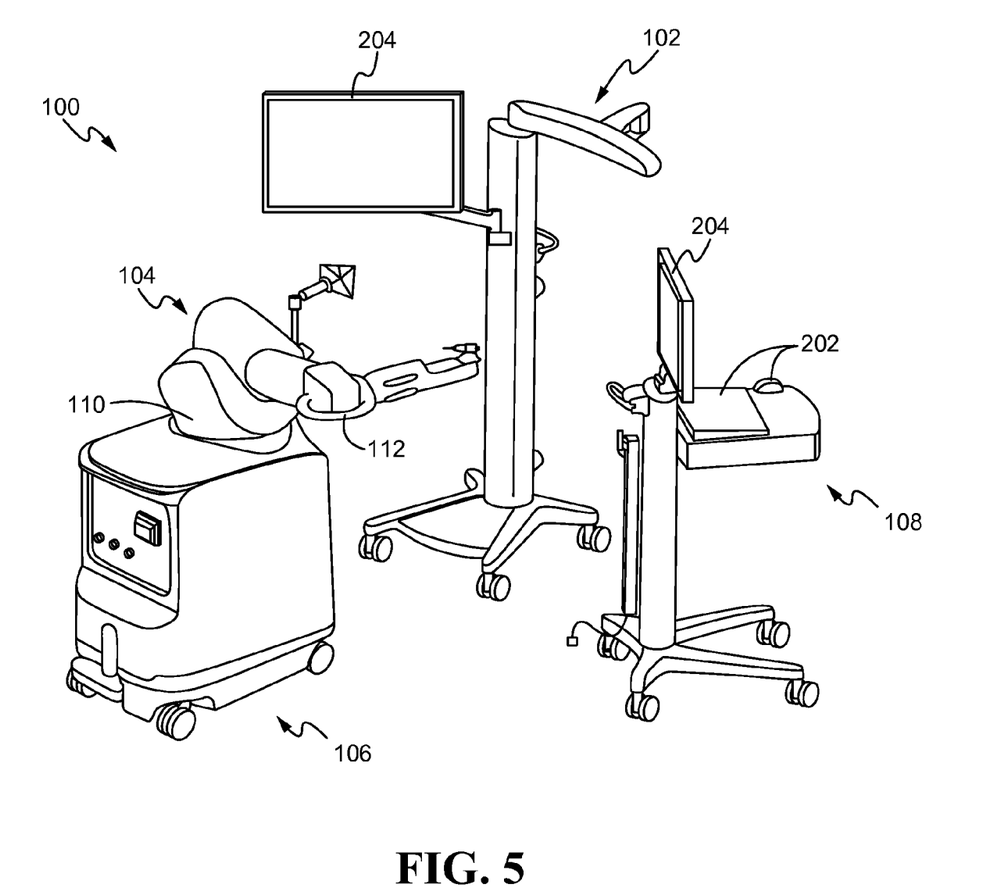
FIG. 5 is a graphical view of one exemplary embodiment of a surgical system configured to determine depth of impaction.

Referring to FIG. 5, one exemplary embodiment of a surgical system 100 is provided. As shown, the surgical system 100 may generally include a tracking device 102, a controllable surgical device 104, a computing device 106 associated with each of the tracking and surgical devices 102, 104, as well as a user interface 108 for interfacing with the computing device 106. The surgical system 100 of FIG. 5 may be used during a surgical procedure involving, for example, a hip joint replacement, or any other suitable procedure involving joint surgery. In particular, the tracking device 102 may track movements of the controllable surgical device 104 and an anatomical region of interest, for example, a diseased hip joint 10 of a patient, while the surgical device 104 may be used to perform a surgical task on the hip joint 10. The computing device 106 may graphically process monitored movements of the surgical device 104 and the hip joint 10 into visual representations or models to be viewed and/or manipulated by a user, such as a surgeon or other operating room personnel, via the user interface 108 while planning or performing a surgical procedure.

The tracking device 102 of FIG. 5 may include means for tracking movement of the anatomical region of interest or hip joint 10. In particular, the tracking device 102 may include a detector and one or more spatially detectable markers that are disposed near an anatomical region of interest. The markers may be positioned at relevant sections of the anatomy, for example, on the pelvis and the femur connected to and forming, at least in part, the hip joint 10 in FIGS. 1 and 2. By tracking markers that are affixed about the hip joint 10, the detector may be able to track any movements, translations, tilts, and the like, within the hip joint 10 and enable the surgeon to compensate for any such shift in movement. The tracking device 102 may additionally include apparatus for tracking the spatial pose of the controllable surgical device 104 relative to the markers and the hip joint 10. As used herein, "pose" means position and orientation. For example, the tracking device 102 may be configured to track a unique identifier on or within the surgical device 104 and/or a working end thereof. Alternatively, information provided by the tracking device 102 may be used in conjunction with the net displacement of the surgical device 104 as detected within a base 110 thereof or by a computing device 106 that may be associated therewith, in order to determine the spatial location of the surgical device 104 relative to the hip joint 10. Based on such tracking techniques and using predefined geometric relationships between the hip joint 10 and the markers, the surgical system 100 may be able to track the spatial pose of the surgical device 104 relative to the markers and thus the hip joint 10.

Figure 6:
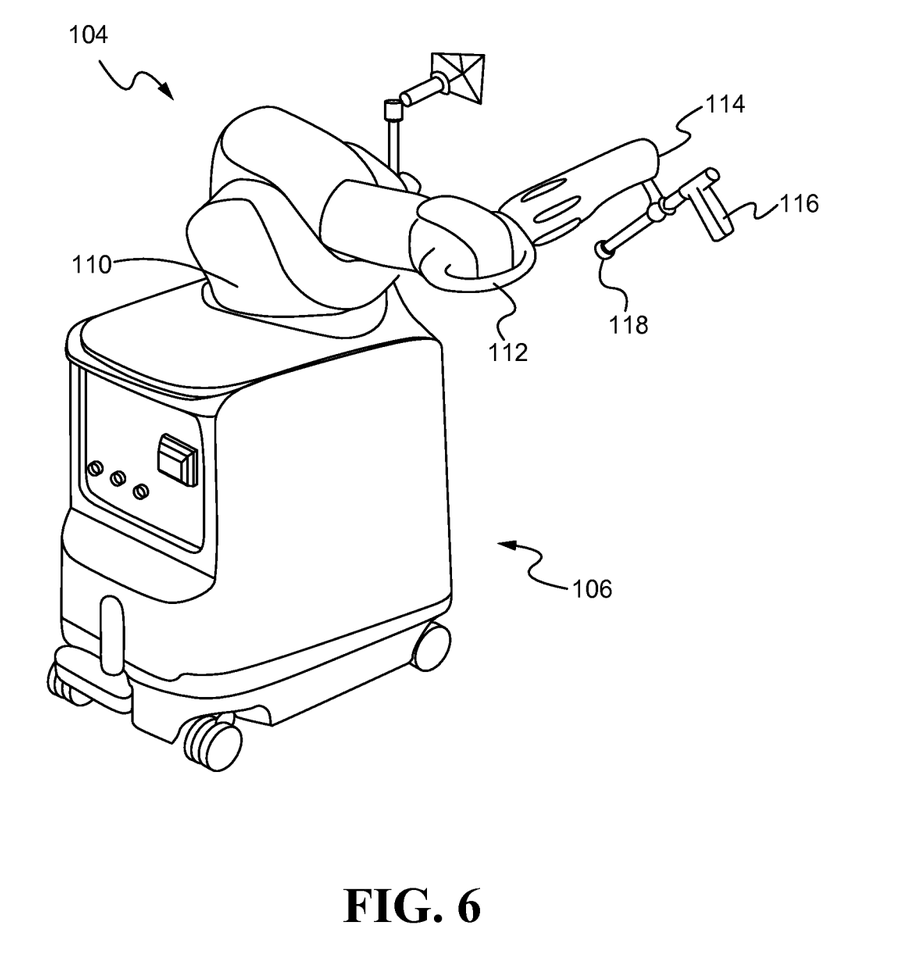
FIG. 6 is a perspective view of one exemplary embodiment of a controllable surgical device configured to determine depth of impaction.
Figure 7:
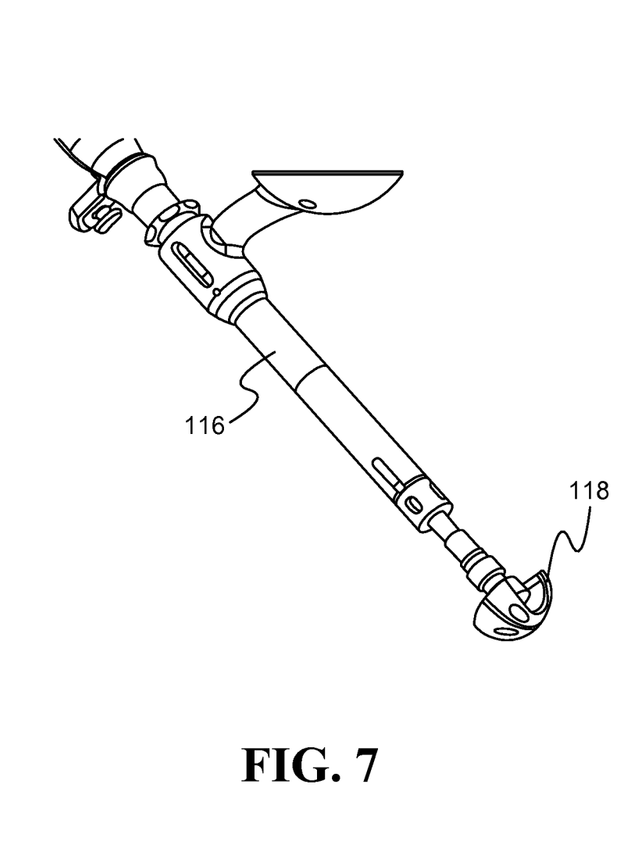
FIG. 7 is a perspective view of one exemplary reamer as applied to an end effector.

As shown in FIG. 6, the controllable surgical device 104 may include a robotic device, such as an articulated arm 112, or the like, that is at least partially monitored and/or controlled by the computing device 106. The articulated arm 112 may be anchored to the base 110 and provided with a working end 114 to which a surgical tool, such as an end effector 116, may be removably coupled. Furthermore, the end effector 116 may be adapted to receive any one of a plurality of operating members enabling the surgical device 104 to be used for a variety of different surgical tasks, such as bone cutting or implant installation. For instance, the end effector 116 of FIG. 7 may be fitted with a cutting element or reamer 118 for reaming a diseased acetabulum 22 and preparing the acetabulum 22 for a prosthetic cup 32. The end effector 116 of FIG. 8 may be fitted with an impactor tool 120 having an impactor shaft 122 with the prosthetic cup 32 connected at a distal end 124 thereof. The pose of the end effector 116 may be manipulated by grasping and manually moving the articulated arm 112 of FIG. 6 relative to its base 110. Optionally, the pose of the end effector 116 and thus movement of the articulated arm 112 may be manipulated through instructions that may be received at the user interface 108 and processed into motor control signals by the computing device 106. The articulated arm 112 may also be provided with a force feedback system, or the like, that may be operated by the computing device 106 and configured to guide or limit manual manipulation of the end effector 116 by the surgeon.

While performing a surgical task on the patient, the surgeon may manually manipulate the end effector 116 and the articulated arm 112 relative to its base 110 and the patient's body. As the surgeon manipulates the surgical device 104, the tracking device 102 may track the location of the end effector 116 and the articulated arm 112, and if provided with a force feedback system, may provide haptic or force feedback to limit the surgeon's ability to move the end effector 116 beyond a predefined virtual boundary. Predefined virtual boundaries may be determined during the planning stages prior to a surgical procedure and registered or mapped to medical images of the patient's anatomy or region of interest so as to enable highly accurate and repeatable bone cuts and/or implant placement. The articulated arm 112 may operate in a passive manner and provide haptic feedback when the surgeon attempts to move the surgical tool beyond the virtual boundary. Haptic feedback may be generated by one or more actuators, such as motors, and the like, within the articulated arm 112 and transmitted to the surgeon via a flexible transmission, such as a cable drive transmission. When the articulated arm 112 is not providing haptic feedback and unless a virtual brake is engaged by the surgeon, the articulated arm 112 may be freely moveable. Actual work on the region of interest may be performed by controlling the surgical device 104 and manipulating the working end 114 of the surgical device 104 to perform surgery, surgical planning and/or surgical navigation, as described, for example, in U.S. patent application Ser. No. 12/894,080, which is hereby incorporated by reference.

Figure 9:
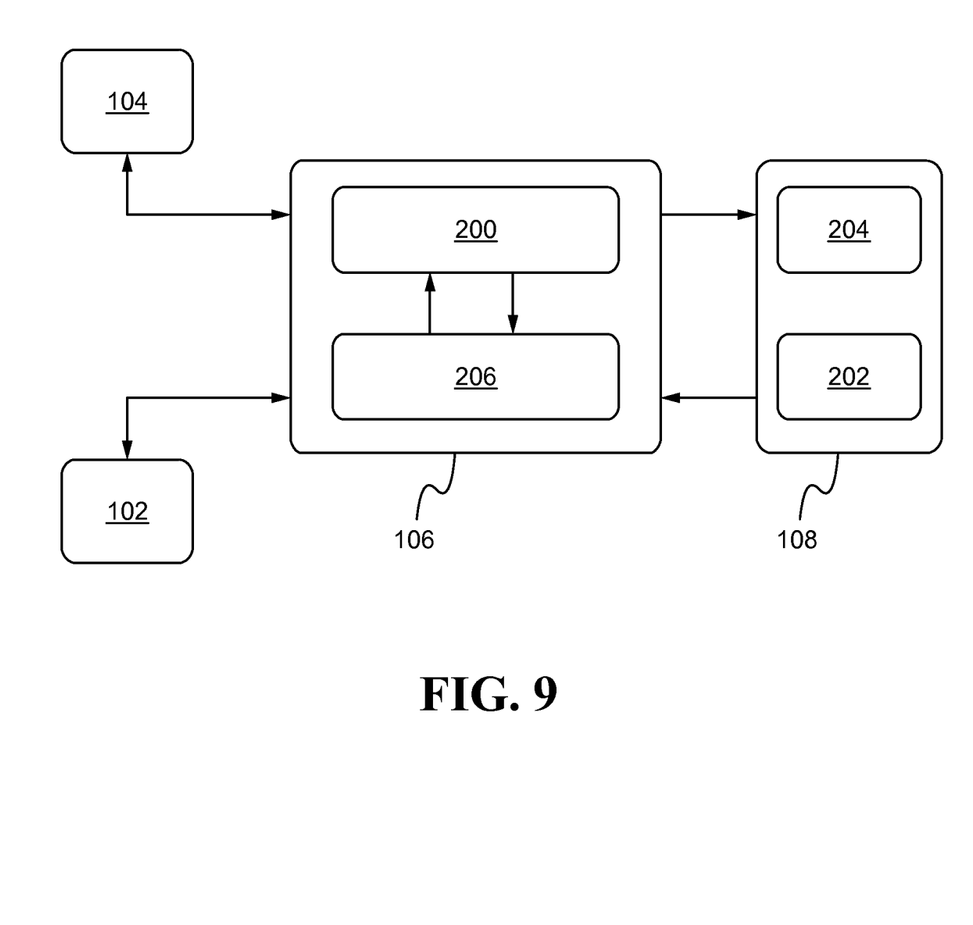
FIG. 9 is a schematic view of one exemplary computing device configured to determine depth of impaction.

Overall progress of a surgical task may be centrally managed by the computing device 106, as schematically illustrated in FIG. 9. More specifically, the computing device 106 may include hardware and software configured to continuously guide the surgeon through a surgical procedure, such as impaction of a prosthetic cup 32 into an acetabulum 22. As shown, the computing device 106 may provide a controller 200 that is in communication with the tracking device 102, the surgical device 104, as well as input and display devices 202, 204 of the user interface 108. The controller 200 may be in wired or wireless communication with one or more of the tracking device 102 and the surgical device 104. The input device 202 may include a keyboard, a mouse, a trackball, a touch screen, a touch pad, a microphone, a dial, a switch, a button, a camera, or any other device suitable for inputting information directly into the controller 200. The display device 204 may include a liquid crystal display (LCD), a cathode ray tube (CRT) display, a plasma screen, a touch screen, and/or any other output device for graphically displaying information processed by the controller 200. The computing device 106 may further include memory 206 for at least temporarily storing one or more medical images of the region of interest, such as the patient's hip joint 10, as obtained by computer tomography (CT) devices, magnetic resonance imaging (MRI) devices, fluoroscopic devices, ultrasound devices, and the like. Based on the medical images, the controller 200 may be able to construct two- or three-dimensional graphical models of the patient's hip joint 10, which may be manipulated by the surgeon via the input device 202 and viewed at the display devices 204. The memory 206 may further be used to store algorithms by which the controller 200 and the computing device 106 may be configured to operate.

Figure 10:
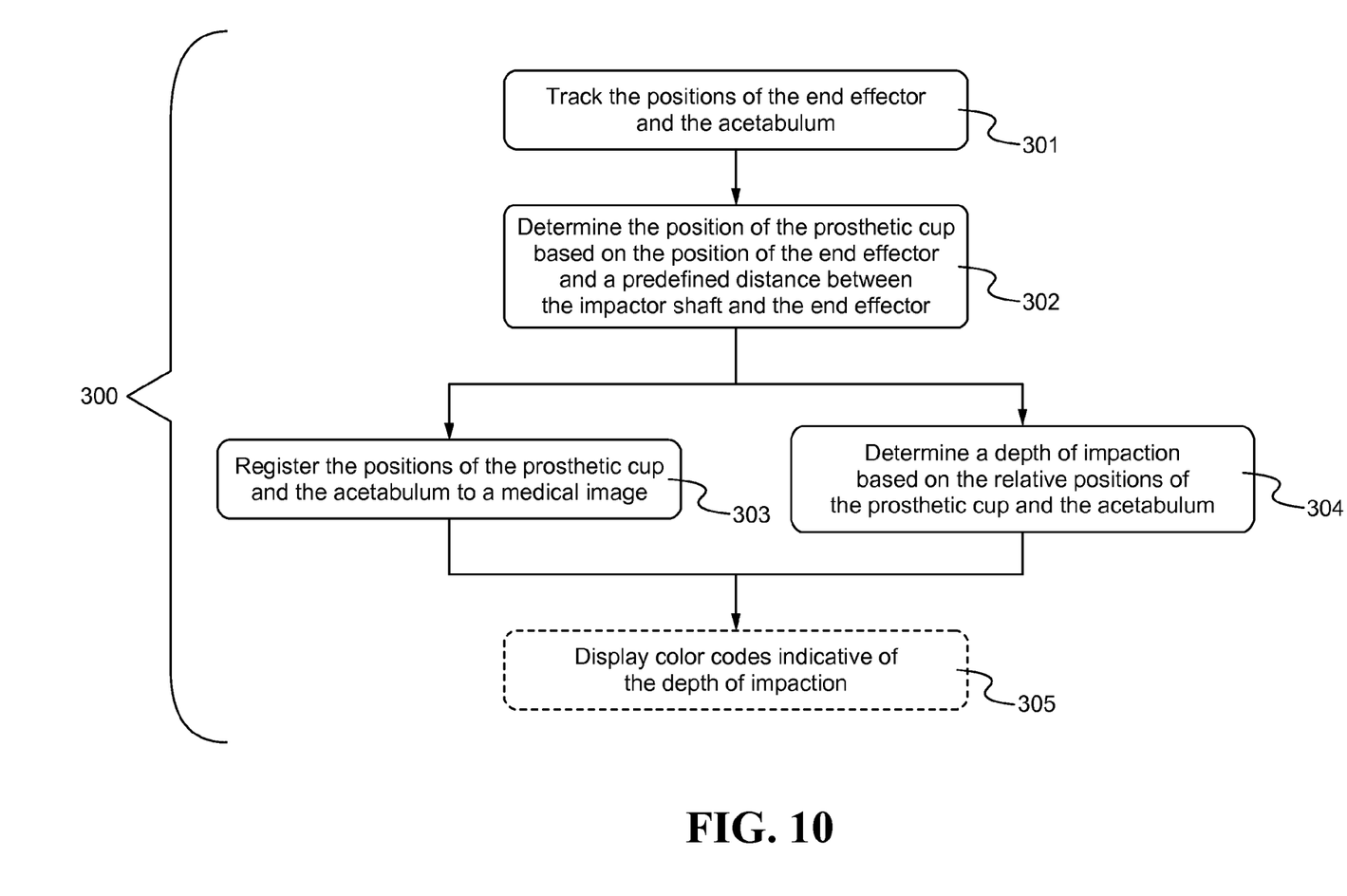
FIG. 10 is a diagrammatic view of one exemplary method for determining depth of impaction.

Turning to the embodiment of FIG. 10, one exemplary algorithm or method 300 by which the controller 200 of the computing device 106 may be configured to operate is provided. Specifically, the method 300 may be preprogrammed into the controller 200 to function according to, for example, steps 301-305 of FIG. 10, so as to determine the depth of impaction during installation of the prosthetic cup 32. As shown, in step 301, the controller 200 may be configured to track the spatial poses of the patient's acetabulum 22 and the end effector 116. In particular, the controller 200 may receive tracking information from the tracking device 102 relating to the spatial poses of markers positioned in the proximity of the patient's acetabulum 22. Based on the marker poses, the controller 200 may be able to deduce the actual corresponding spatial pose of the acetabulum 22. The controller 200 may similarly process tracking information relating to the spatial poses of one or more markers or identifiers positioned on the end effector 116 to deduce the actual corresponding spatial pose of the end effector 116. The controller 200 may alternatively or additionally determine the spatial pose of the end effector 116 based on a net detected displacement of the joints of the attached articulated arm 112 with respect to its base 110.

Figure 8:
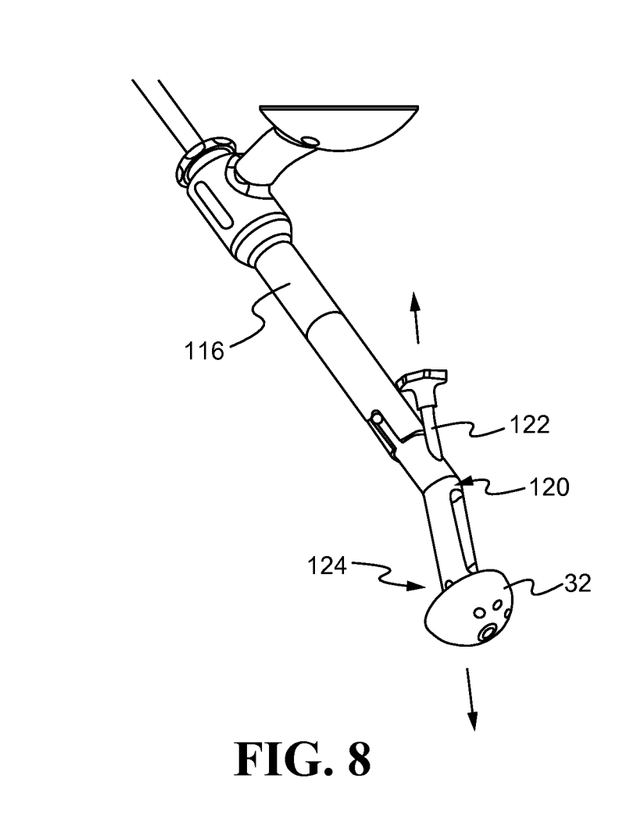
FIG. 8 is a perspective view of one exemplary impactor tool as applied to an end effector.

In step 302, the controller 200 may be configured to determine the spatial pose of an attached prosthetic cup 32 using at least the spatial pose of the end effector 116 determined from step 301. More specifically, once the spatial pose of the end effector 116 has been established, the spatial pose of the attached prosthetic cup 32 may be determined based on a known pose between the end effector 116 and the prosthetic cup 32. As shown in FIGS. 4 and 8, the prosthetic cup 32 may be attached to the distal end 124 of the impactor shaft 122, which is further coupled to the end effector 116. Furthermore, as the impactor shaft 122 may be slidably movable along its axis and relative to the end effector 116, the distance between the end effector 116 and the prosthetic cup 32 may be variable. Accordingly, for the purposes of capturing the depth of impaction, the impactor shaft 122 may be temporarily moved to a predetermined default position such that in the default position, the pose between the end effector 116 and the attached prosthetic cup 32 may be known. For example, prior to each depth of impaction measurement, the surgeon may extend or retract the impactor shaft 122 into the default position such that the pose between the prosthetic cup 32 and the end effector 116 is always consistent. By maintaining the default position and as long as the spatial pose of the end effector 116 is known, the controller 200 may determine the spatial pose of the prosthetic cup 32 relative to the acetabulum 22 without individually tracking the prosthetic cup 32. Alternatively, the controller 200 may be able to track the pose of impactor shaft 122 relative to the end effector 116. This may be accomplished, for example, by associating a linear encoder with the impactor shaft 122, such that the controller 200 can determine the pose of the distal end of the impactor shaft 122 relative to the end effector 116 and determine the pose of the prosthetic cup 32 relative to the acetabulum 22. In yet another alternative embodiment, the impactor shaft 122 may be rigidly fixed relative to the end effector 115; however, this embodiment would require a relatively rugged articulated arm 112 to absorb the forces and vibrations created by striking a rigidly attached impactor shaft 122 without affecting calibration.

In step 303, the controller 200 may be configured to register or map the spatial pose of the acetabulum 22 determined from step 301 and the spatial pose of the prosthetic cup 32 determined from step 302. More specifically, the tracked pose of the actual acetabulum 22 may be registered to the corresponding pose within a medical image, such as a CT scan, or any other suitable graphical representation or model of the hip joint 10. Upon registering the location of the acetabulum 22 to the model, the controller 200 may similarly register the tracked pose of the prosthetic cup 32 onto the model based on previously determined spatial relationships. For example, based on the spatial relationship between the prosthetic cup 32 and the acetabulum 22 determined in step 302, and using the registered model pose of the acetabulum 32 as a starting point, the controller 200 may be able to locate the pose within the model that corresponds to the prosthetic cup 32. Once the tracked pose of the prosthetic cup 32 is registered to the model, an image representing the prosthetic cup 32 may further be superimposed onto the model containing the acetabulum 22, as shown for example in FIGS. 11-13.

In step 304, the controller 200 may be configured to determine the depth of impaction or, as shown in FIG. 4, the depth D which remains between the prosthetic cup 32 and the acetabulum 22. As shown, the depth of impaction D may be calculated by measuring the distance from the distal end 124 of the impactor shaft 122 to the deepest center position 126 of the prosthetic cup 32. To determine the spatial pose of the distal end 124, or where the associated prosthetic cup 32 is situated, the controller 200 may employ the spatial relationship determined in step 302. The deepest center position 126 of the prosthetic cup 32 may be derived based on a surgical plan conducted prior to the impaction process. The deepest center position 126 may further be determined based on the trajectory of a reamer 118 previously used to ream and prepare the acetabulum 22 for the prosthetic cup 32. For instance, the controller 200 may employ previously recorded or tracked reamer trajectory points to determine the optimum location of the prosthetic cup 32 and the deepest center point 126 corresponding thereto. In cases where the reamer 118 and the prosthetic cup 32 substantially similar with respect to geometry and trajectory, the deepest center position 126 of the reamer 118 may correspond directly to that of the prosthetic cup 32. Alternatively, in cases where the reamer 118 and the prosthetic cup 32 have different geometries and/or trajectories, the calculated depth of impaction D may be adjusted to correct for the differences.

Figure 11:
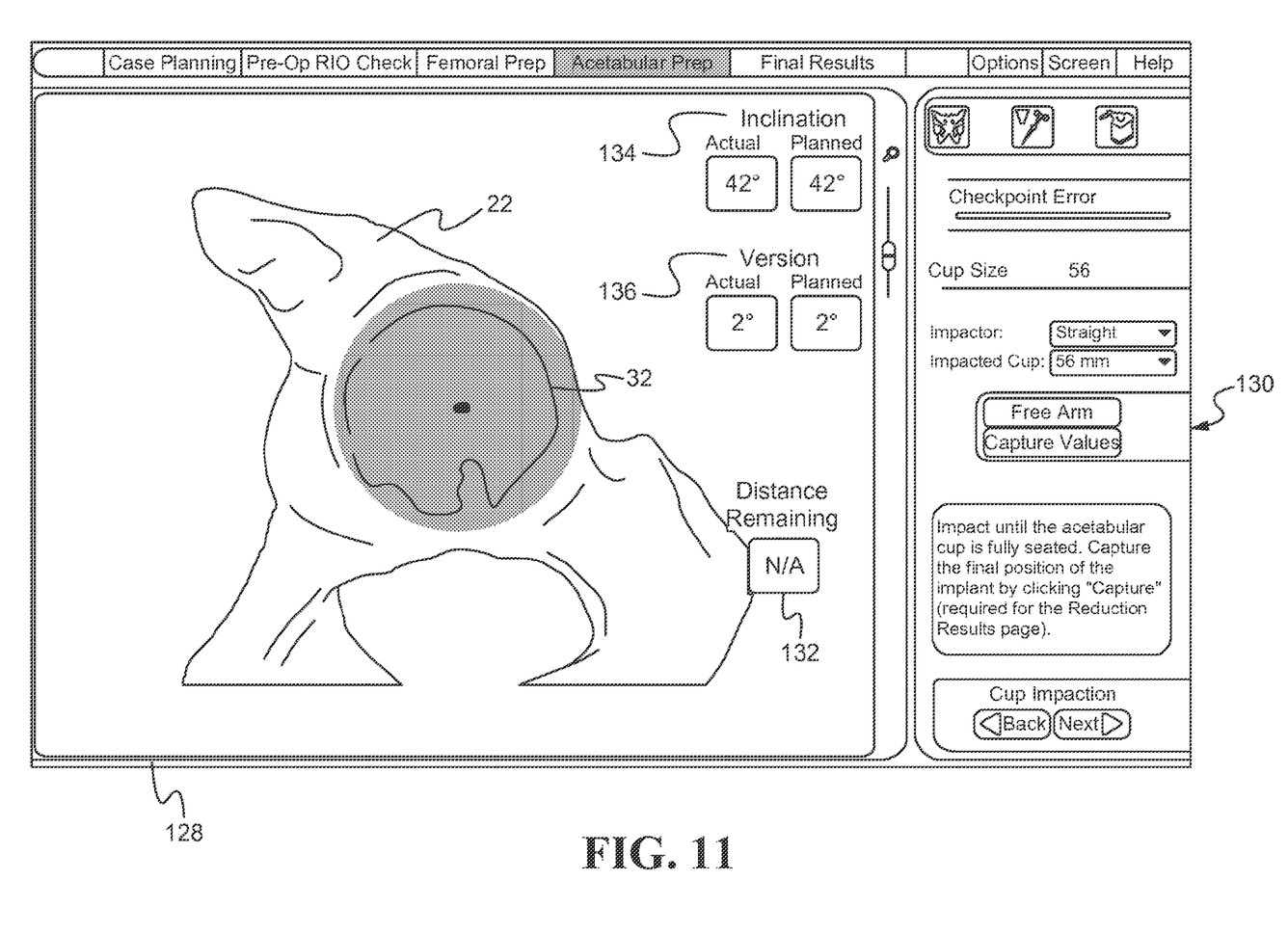
FIG. 11 is a graphical view of one exemplary display as provided by the present disclosure.
Figure 12:
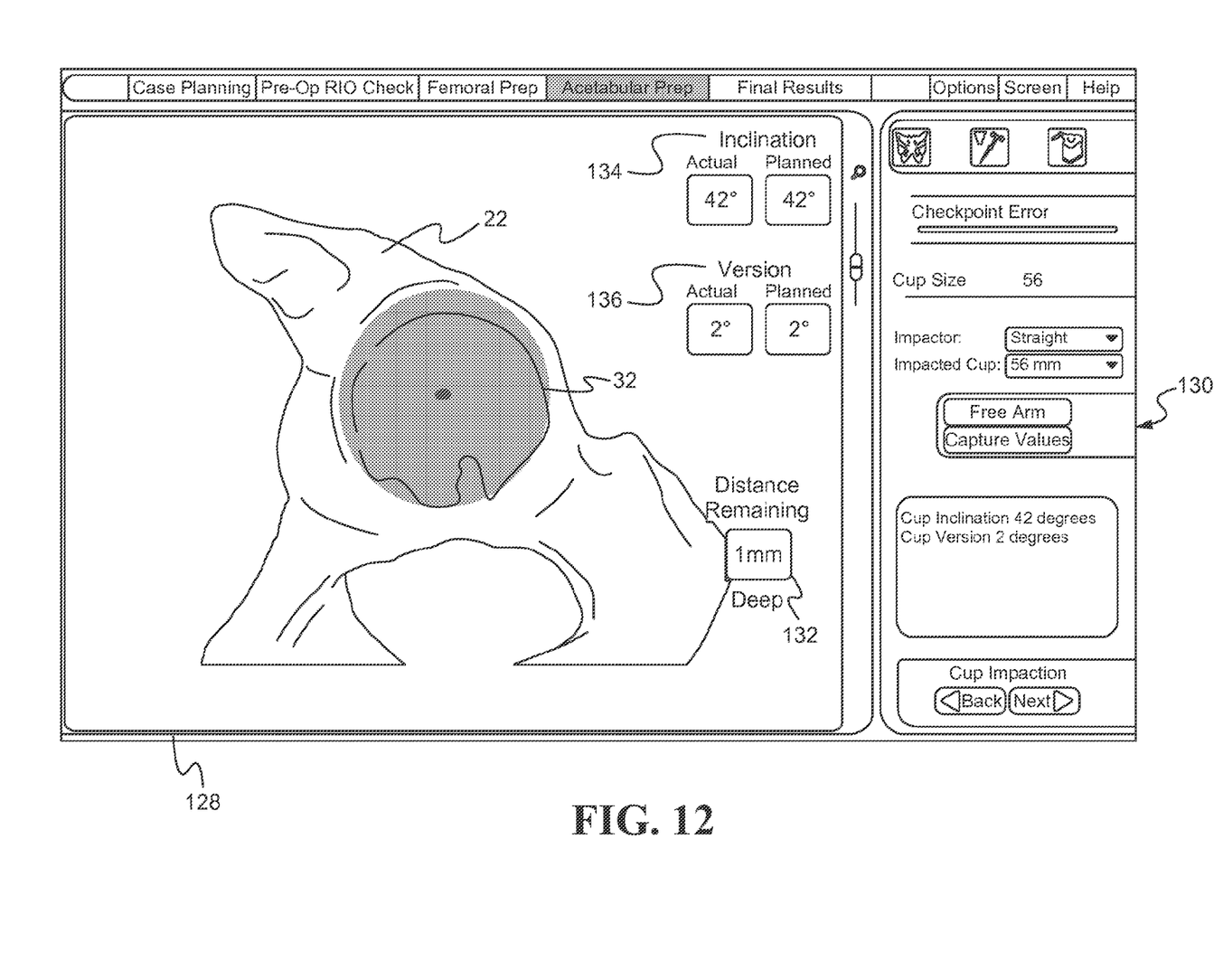
FIG. 12 is a graphical view of another exemplary display as provided by the present disclosure.
Figure 13:
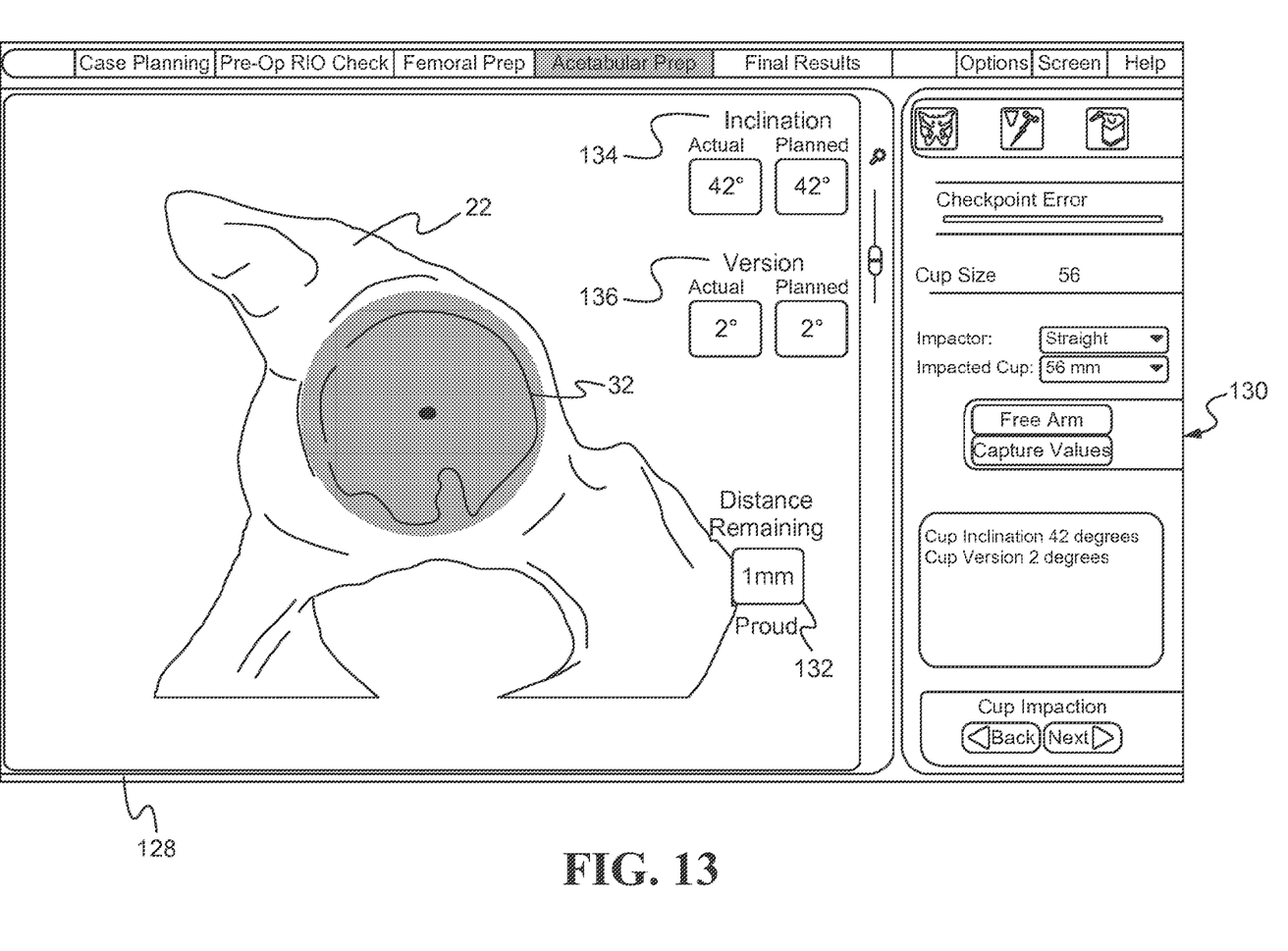
FIG. 13 is a graphical view of another exemplary display as provided by the present disclosure.

Once registrations in step 303 are complete, the controller 200 may provide displays 128, as shown in FIGS. 11-13, at one or more display devices 204 so as to visually indicate to the surgeon the current depth of the prosthetic cup 32 or the depth still remaining until the appropriate depth is reached. The controller 200 may also be configured to receive input from the surgeon via one or more input devices 202 so as to enable manipulation of the models presented and/or modification to the parameters thereof. For instance, the surgeon may rotate, translate, resize, zoom into or out of the particular view displayed, and/or make any other adjustments to the graphical representations provided. The surgeon may also modify input values and parameters, such as the planned inclination value, the planned version value, the cup size, the impactor type, and the like. The displays 128 may also provide a control menu 130 through which the surgeon may instruct the controller 200 to perform certain operations, such as capturing values, freeing control of the articulated arm 110, and the like.

In addition to providing a visual representation of the prosthetic cup 32, the display 128 may also provide a section 132 for the displaying the actual depth of impaction or distance remaining as determined from step 304. Moreover, the controller 200 may be configured to color code the display 128 to better indicate the progress of the impaction to the surgeon. For example, the display 128 may color code the depth of impaction section 132 in green if the depth D determined in step 304 indicates that the prosthetic cup 32 is more than 1 mm away from the desired or planned depth. The green color code may serve to indicate to the surgeon that it is safe to continue impaction. The depth of impaction section 132 of the display 128 may also be color coded in white if the determined depth D is within 1 mm from the planned depth to indicate to the surgeon to proceed slowly with caution. Further, the depth of impaction section 132 of the display 128 may be color coded in red if the determined depth D indicates that the prosthetic cup 32 is deeper than the planned depth. The red color code may serve to indicate to the surgeon to stop impaction and/or retract the prosthetic cup 32 accordingly. Alternatively, the controller 200 may be configured to apply different color coding schemes for different ranges of impaction.

The displays 128 of FIGS. 11-13 may further provide sections 134, 136 for the actual inclination and version values of the prosthetic cup 32 as compared to planned values. As with the depth of impaction section 132, the inclination and version sections 134, 136 may also be color coded to better indicate when the actual values, indicative of the pelvic tilt, stray from the planned values. For instance, the controller 200 may be configured to color code the actual inclination and version sections 134, 136 of the display 128 in red if the values are at all removed from their respective planned values. Additionally, the controller 200 may color code the actual inclination and version sections 134, 136 in green if the values return to their respective planned values. In alternative modifications, the controller 200 may be configured to apply different color combinations for different monitoring schemes.

While only certain embodiments have been set forth for the purposes of illustration, alternatives and modifications will be apparent from the above description to those skilled in the art. These and other alternatives are considered equivalents and within the spirit and scope of this disclosure and the appended claims.

What is claimed is:

1. A method for determining a depth of impaction of a prosthetic cup into an acetabulum, the method comprising the steps of:
   positioning the prosthetic cup at a distal end of an impactor shaft that is slidably movable relative to an end effector;
   tracking a spatial pose of the end effector relative to a spatial pose of the acetabulum;
   positioning the impactor shaft to a known ose relative to the end effector;
   determining a spatial pose of the prosthetic cup based on the spatial pose of the end effector and the known pose between the distal end of the impactor shaft and the end effector; and
   determining the depth of impaction based on the spatial pose of the prosthetic cup and the spatial pose of the acetabulum.

2. The method of claim 1, wherein the spatial pose of the end effector and the spatial pose of the acetabulum are registered to at least one medical image of the acetabulum.

3. The method of claim 1, wherein the depth of impaction is measured as a distance along an axis of the impactor shaft and between a current depth of the distal end and a projected depth of the distal end.

4. The method of claim 1, wherein inclination and version of the prosthetic cup are determined based on the spatial pose of the acetabulum and a planned pose of the prosthetic cup.

5. The method of claim 1 further comprising the step of displaying color codes indicative of the depth of impaction.

6. The method of claim 1 further including the step of determining a trajectory of a reamer used to ream the acetabulum.

7. The method of claim 6, wherein the step of determining the depth of impaction is further based on the trajectory of the reamer used to ream the acetabulum.

8. The method of claim 7, wherein the step of determining the depth of impaction is further based on a difference between the geometry of the reamer and the geometry of the prosthetic cup.

9. The method of claim 7, wherein the step of determining the depth of impaction is further based on a difference between the trajectory of the reamer and the trajectory of the prosthetic cup.

* * * * *